United States Patent [19]

Bledsoe et al.

[11] Patent Number: 5,601,089
[45] Date of Patent: Feb. 11, 1997

[54] METHOD AND APPARATUS FOR BOOSTING THE AMPLITUDE OF ECG SIGNALS WITHIN A PREDETERMINED FREQUENCY RANGE

[75] Inventors: J. Daren Bledsoe; David L. Burton; Brian D. Setterberg; Alan V. Andresen, all of McMinnville, Oreg.

[73] Assignee: Hewlett-Packard Company, Palo Alto, Calif.

[21] Appl. No.: 379,046

[22] Filed: Jan. 26, 1995

Related U.S. Application Data

[62] Division of Ser. No. 31,437, Mar. 12, 1993, Pat. No. 5,406,955.

[51] Int. Cl.$^6$ ........................................... A61B 5/0436
[52] U.S. Cl. ........................................... 128/711
[58] Field of Search ........................ 128/696, 697, 128/710, 711, 902

[56] References Cited

U.S. PATENT DOCUMENTS

| | | | |
|---|---|---|---|
| 3,721,230 | 3/1973 | Zigmicki | 128/710 |
| 3,871,363 | 3/1975 | Day | 128/697 |
| 4,098,267 | 7/1978 | Stein et al. | 128/711 |
| 4,291,703 | 9/1981 | Kelen | 128/711 |
| 4,333,475 | 6/1982 | Moreno et al. | 128/711 |
| 4,422,459 | 12/1983 | Simson | 128/702 |
| 4,457,315 | 7/1984 | Bennish | 128/704 |
| 4,494,551 | 1/1985 | Little, III et al. | 128/696 |
| 4,532,934 | 8/1985 | Kelen | 128/697 |
| 4,580,576 | 4/1986 | Blackwood | 128/711 |
| 4,585,201 | 1/1986 | Lass | 128/696 |
| 4,624,263 | 11/1986 | Slavin | 128/710 |
| 4,630,204 | 12/1986 | Mortara | 364/417 |
| 4,680,708 | 7/1987 | Ambos et al. | 364/417 |
| 4,696,306 | 9/1987 | Shiozaki | 128/711 |
| 4,721,114 | 1/1988 | DeFault et al. | 128/696 |
| 4,883,065 | 11/1989 | Kelen | 128/711 |
| 4,961,428 | 10/1990 | Nikias et al. | 128/699 |
| 5,030,911 | 7/1991 | Lam | 324/226 |
| 5,050,021 | 9/1991 | Shu et al. | 360/95 |

OTHER PUBLICATIONS

Service Manual For Holter Acquisition Module, "Preliminary", Marquette Electronics Inc., Jun. 15, 1993, pp. 9–11.
Jorgensen, The Complete Handbook of Magnetic Recording (3rd Edition) 1998, pp. 492–497.
Woram, The Recording Studio Handbook, 1980, p. 279.
Oppenheim, Digital Signal Processing, 1975, p. 19.
Mazade et al, "Medical & Biological Engineering & Computing" vol. 17, 1979, pp. 683–687, copy in 128/711.
"The Recording Studio Handbook", John M. Woram, Sagamore Publishing Company, Inc., Apr., 1980, pp. 327–331.

*Primary Examiner*—William E. Kamm
*Attorney, Agent, or Firm*—Curtis G. Rose

[57] ABSTRACT

An ECG recorder and playback unit which includes software-implemented digital signal processing filters which compensate for phase and magnitude distortion occurring when an ECG signal is recorded on a Holter recorder and played back. This permits "tuning" a recorder and playback unit which may be unrelated, as when made by different manufacturers. An impulse or step signal is recorded and played back to provide a system frequency response measurement. Coefficients for a digital correction filter are derived from the discrete Fourier transform of the impulse or step response and a desired system response. When recorded ECG data is played back, it is filtered on a substantially real-time basis with the digital correction filter to compensate for phase and magnitude distortion. Prior to recording, the high frequencies of the ECG signal are boosted to compensate for high frequency losses inherent in the recording and playing back of ECG signals. A calibration pulse and a system characterization pulse are derived by statistically selecting from a plurality of pulses and averaging the selected pulses in order to minimize the effects of noise and tape defects in the pulses. High frequency components of the ECG signal can be amplified prior to recording the signal. This results in decreased amplification, and therefore noise, when the recorded signals are played back. Cardiac pacer pulse detection is performed prior to the step of filtering the played back signal to optimize pulse detection.

5 Claims, 4 Drawing Sheets

METHOD AND APPARATUS FOR BOOSTING THE AMPLITUDE OF ECG SIGNALS WITHIN A PREDETERMINED FREQUENCY RANGE

This is a divisional of application Ser. No. 08/031,437 filed on Mar. 12, 1993, now U.S. Pat. No. 5,406,955.

BACKGROUND OF THE INVENTION

1. Field of the Invention

The present invention relates to methods and apparatus for recording and playing back ECG signals and more particularly to such methods and apparatus in which the ECG signals are processed to remove phase and magnitude distortion occurring during the recording and playback process.

2. Description of the Related Art

Prior art systems, known as Holter recorders, record ECG signals which are provided from a patient via electrodes to a small recorder carried by the patient. The ECG signals are continuously recorded on an analog tape typically over a 24 hour period. Several prior art systems use a conventional C60 analog cassette tape of the type typically used to record audio information. In order to do so, the tape must be slowed down approximately 50 times from normal audio speeds. Usually three channels of ECG data are recorded plus a fourth channel which includes a timing signal that is generated by the recorder.

After recording, the tape is played back on a device which runs the tape at high speed and processes the analog signals derived from the tape. Such processing typically includes analog filters which are intended to compensate for dropoff at both the low and high frequencies and for phase distortion which results from the magnetic recording and playback process. The filtered signals are digitized and further processed into a report for analysis by a physician.

As used herein, the term magnitude response refers to the manner in which a system for recording and playing back an ECG signal affects the magnitude of a signal as the signal frequency varies. The term phase response refers to the manner in which such a system affects the phase of a signal as the signal frequency varies. Magnitude response and phase response are referred to herein collectively as frequency response. An ideal system for recording and playing back ECG signals would have a substantially flat magnitude response and a linear phase response. Analog tape recording technology of the type described above suffers from several limitations which adversely affect both the magnitude and the phase response of prior art systems for recording and playing back ECG signals. Because the playback head on a device for scanning (i.e., playing back) recorded ECG signals detects only the rate of change of tape flux, there is no magnitude response at DC. The playback head in essence differentiates signals on the tape. This differentiation has the effect of phase shifting signals positive 90 degrees and attenuating low frequency signals. To recover the original information, the playback unit must integrate the output signal from the playback head. This integration process compensates for the differentiation by providing negative 90 degrees phase shift and amplification of low frequencies. In prior art systems, the integration process results in phase distortion and excessive amplification of low frequency noise (baseline wander).

High frequency magnitude response of the playback signal tends to drop off due to the physical limits of the playback head, recording head inductance, tape coating effects and also as a result of the slow rate of tape transport during recording. This effect may be compensated for by boosting the played back signal in the high frequencies. This has the effect of increasing both signal and noise in this range. Recent research indicates that there is clinically important information which can be obtained from an ECG signal above 40 Hz; increased noise in this range is therefore undesirable.

As mentioned above, prior art systems filter the signal derived from a tape playback head during scanning of the recorded tape in an effort to compensate for phase and magnitude distortion. Such systems suffer from several disadvantages. First, analog filters are not as accurately implemented as a digital filter due to variations in component tolerance. In addition, analog filters are subject to drift. More importantly, prior art analog filters are relatively fixed in the manner in which they compensate. In other words, a fixed phase and magnitude distortion is assumed in the system for recording and playing back the signal. An analog filter is designed which compensates for the assumed distortion. One problem with this approach is that phase and magnitude distortion produced by a system for recording and playing back ECG signals varies over time. It can vary as a result of wear on the heads for recording and playing back the signal. It can also vary in response to misalignment of the mechanical components which affect the record and playback head compliance with the tape. If the recorder is not matched with the playback unit, e.g., if they are made by different manufacturers, the filter may not compensate properly. Different recorders will therefore produce different results when the recorded data is played back on the same playback unit. Independently of time, distortion can vary as a result, e.g., of using an analog tape having a different thickness or type of tape coating thereon.

Prior art techniques for calibrating the ECG recorder include recording a series of rectangular calibration pulses of known amplitude on each of three channels used for recording ECG signals. Pulses are played back through a playback deck and passed through analog compensation filters to restore the pulse's original phase and frequency content. The playback unit is calibrated by measuring the amplitude of the calibration pulses and thereafter generating a data scaler which is applied to the ECG data.

There are several problems with this approach. One is that phase and magnitude distortion can vary from channel to channel. Also, generating a data scaler does not compensate phase and magnitude over frequency. Another problem results from a phenomenon called tape dropout. Tape dropout is an apparent reduced recording level on a tape caused by variations in the recording medium. When such areas are encountered during the calibration process, accuracy of calibration is adversely affected.

SUMMARY OF THE INVENTION

The present invention provides a method and apparatus for processing ECG data which is collected by a system for recording and playing back the data. In performing the method, a system frequency response is measured. Then, a correction filter response is derived from the system frequency response and a predetermined desired frequency response. ECG data is recorded and played back using the system. The played-back ECG data is filtered with the correction filter response. In another aspect of the invention, the filtering is done using digital signal processing techniques on a substantially real-time basis by digitizing the data, dividing the digitized data into predetermined block sizes and thereafter forward and reverse filtering each block of data.

In another aspect of the invention, high frequency components of the ECG signal are boosted prior to recording the same on an analog tape. This pre-emphasis scheme compensates for the losses of the recording and playback processes without requiring increased gain in amplifiers for the played-back signal which also amplify noise inherent in the playback amplifiers and magnetic tape.

In another aspect of the invention, calibration pulses are statistically selected and averaged in order to reduce the effects of noise and tape dropout on the calibration process.

In another aspect of the invention, cardiac pacer pulses are detected prior to filtering the recorded ECG signals to compensate for magnitude and phase distortion. The accuracy and ease of pacer pulse detection is improved when done on differentiated data prior to filtering.

In another aspect, a characteristic such as frequency response or time base error, is measured. An acceptable range for the measurement is defined and a system operator is alerted when the measurement falls outside of the range.

It is a general object of the present invention to provide an ECG recorder and playback unit and method which overcomes the above-enumerated disadvantages associated with prior art systems and methods.

It is another object of the present invention to compensate played-back ECG signals for phase and magnitude distortion occurring as a result of the recording and playback process.

It is another object of the present invention to compensate for such distortion utilizing digital signal processing techniques on a substantially real-time basis.

It is another object of the present invention to boost the high frequencies of the ECG signal prior to recording the signal.

It is another object of the present invention to generate an averaged input characterization pulse for determining a system transfer function that is used to derive a correction filter response.

It is another object of the present invention to generate an average calibration pulse to improve system calibration.

It is another object of the present invention to detect cardiac pacer pulses prior to ECG signal compensation filtering.

It is another object of the present invention to verify system performance for each procedure.

It is another object of the present invention to provide adaptable filter parameters and to permit either selective or automatic reconfiguration of filter parameters.

It is another object of the present invention to permit using recorders which are not matched with the playback unit and which may even be made by different manufacturers.

It is another object of the present invention to permit a user to set or adjust the low and high frequency system response.

It is another object of the present invention to minimize baseline wander while preserving low frequency phase of the played back ECG signal.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENT

Figure 1:
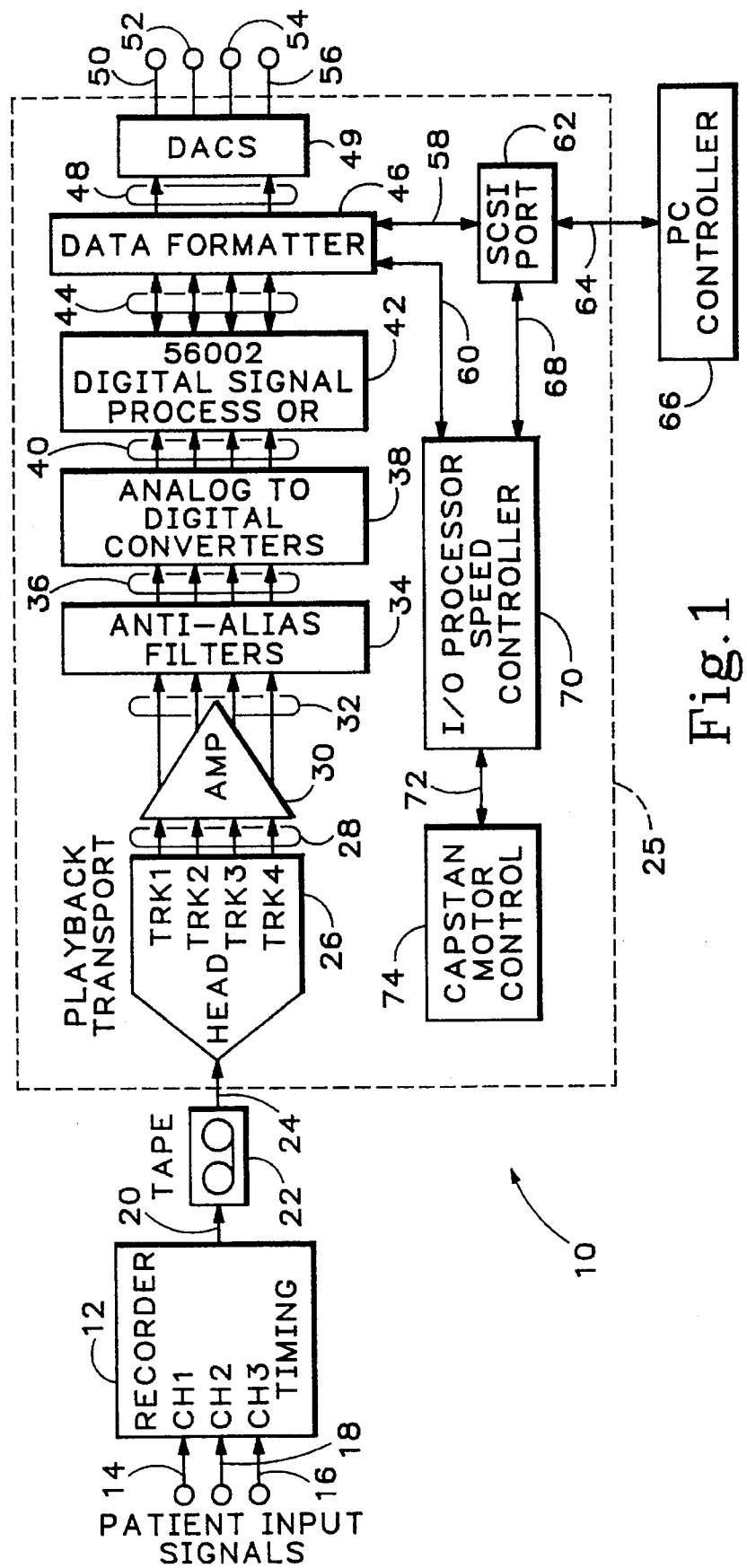
FIG. 1 is block diagram of a Holter recorder and playback unit.

Referring to FIG. 1, a Holter recorder and playback unit is shown generally at 10. The system comprises a portable Holter recorder 12 for recording ECG patient signals received over patient monitor lines 14, 16, and 18, which are typically connected to patch-type electrodes affixed to the patient's skin. A different ECG signal is provided on each of the three lines. Recorder 12 is desirably a miniature recorder worn on the patient's belt in order to collect data over an extended period of time. The portable Holter recorder 12 also includes means for generating and recording a repetitive characterization signal (not shown in FIG. 1 and explained in greater detail below).

The ECG patient signals and characterization signal are processed within recorder 12 to produce recorder signals 20 capable of being stored on a standard magnetic cassette tape 22 held in the recorder 12. Each of the three ECG signals is recorded onto separate tracks of the magnetic cassette tape 22, e.g., tracks 1, 2 and 4. As will be described shortly, a characterization signal may also be recorded on the tape tracks prior to recording the ECG signals. A timing signal is recorded onto yet another separate, track 3. The timing signal is a constant frequency signal which creates timing information on tape 22. In addition, a patient activated signal, created by depressing a switch, can be captured on the timing track.

After EGG signals are recorded on tape 22, it is removed from recorder 12 and installed in a playback transport system 25. Each of the four recorded tracks are played back by playback unit 25 which includes a playback transport and post processing circuitry, as well as computer control interface and testing outputs. A playback head 26 converts the information stored on each of the four tracks on magnetic tape 22 into four separate analog playback signals which are applied to analog track lines 28. Each track line corresponds to one of four separate tracks on the tape 22. The circuitry contained in each of blocks 30, 34, 38, and 42, described below, is replicated for each track although separate blocks for each channel are not shown in FIG. 1 to simplify the drawing. Although the preferred embodiment shown in FIG. 1 uses a four track tape, any reasonable number of tracks and patient inputs can be used.

The analog track lines 28 are connected to playback amplifiers 30. The playback amplifiers 30 amplify the analog recorded signals on analog track lines 28 to produce amplified analog signals on amplifier output lines 32. The amplifier output lines 32 are connected to anti-alias filters 34 which act essentially as low pass filters having a corner frequency of about 200 kHz. In the preferred embodiment the anti-alias filters 34 are implemented using conventional R-C networks. The filtered analog signals produced by the anti-alias filters 34 are coupled to analog-to-digital converters ("ADCs") 38 over filter output lines 36 connected between the anti-alias filters 34 and ADCs 38. Analog-to-digital converters 38 also have anti-alias filters with a corner frequency of about 50 kHz.

The analog signals received by ADCs 38 are converted into a digital representation for subsequent digital processing by digital signal processors ("DSP") 42. In the preferred embodiment, each of the analog-to-digital converters is a 56ADC16 manufactured by Motorola of Phoenix, Ariz. The ADCs 38 produce digital outputs on busses 40 which are connected to digital signal processors 42. Each of the digital outputs is a 16-bit sample value which is applied to bus 40 at a rate of 100,000 samples/second. The digital signal processors 42 includes a separate signal processor dedicated to each track. Each of the digital signal processors, in the preferred embodiment, is a 56002 DSP also manufactured by Motorola. The digital signal processors perform the necessary digital processing, as is hereinafter explained, of the digital output, as required by the invention, to produce processed digital data on DSP bi-directional output busses 44.

Data formatter 46 is coupled between DSP 42 and digital-to-analog-converters ("DACs") 49. The DSP bidirectional output busses 44 of the DSP 42 are connected to data formatter 46. Data formatter 46 is connected to DACs 49 through two serial data lines 48. Two of the processed digital outputs 44 are multiplexed onto each of the serial data lines 48 by data formatter 46. The serial data lines 48 are coupled to DACs 49 which produce analog outputs 50, 52, 54, and 56. The analog outputs 50, 52, 54, and 56 can be used as test points or for other purposes. In the preferred embodiment, DACs 49 are multiplexing "dual DACs", C54328 manufactured by Crystal Semiconductor of Austin, Tex. The data formatter 46 also operates as a gateway between a SCSI (small computer systems interface) port 62 and DSP 42.

Data formatter 46 operates under the control of an I/O processor 70. The data formatter 46 is connected to the I/O processor 70 through an I/O bus 60. I/O processor 70 is further connected to a SCSI port 62 through SCSI control bus 68 and to capstan motor control 74 through capstan control bus 72. I/O processor 70 configures data formatter 46 in response to commands sent or received through SCSI port 62. The commands comply with the industry standard SCSI protocol, which governs transfers across SCSI data bus 64 connected between SCSI port 62 and PC controller 66. The commands specify the transfer attributes including: the type of transfer, i.e., read or write; the source and destination addresses; and the corresponding number of bytes. The I/O processor 70 configures data formatter 46, by writing to registers within data formatter 46, in order to accomplish the transfer specified by the command.

SCSI port 62 is coupled to PC controller 66 across SCSI bus 64. PC controller 66 is able to receive processed digital data from DSP 42 across SCSI bus 64 as well as send configuration information to DSP 42 across SCSI bus 64. The PC controller 66 can perform further processing, if necessary, on the processed digital data and display, print or store the resulting output. In addition to the EGG patient signals, the PC controller 66 also receives the characterization signal. The characterization signal received in the processed digital data is examined by the PC controller to determine the compensation required by DSP 42. The PC controller 66 transmits filter coefficients via SCSI bus 64 to DSP 42 in order to accomplish the required compensation, as is described in greater detail below. Digital signal processing can be allocated between DSP 42 and the PC controller 66.

Figure 2:
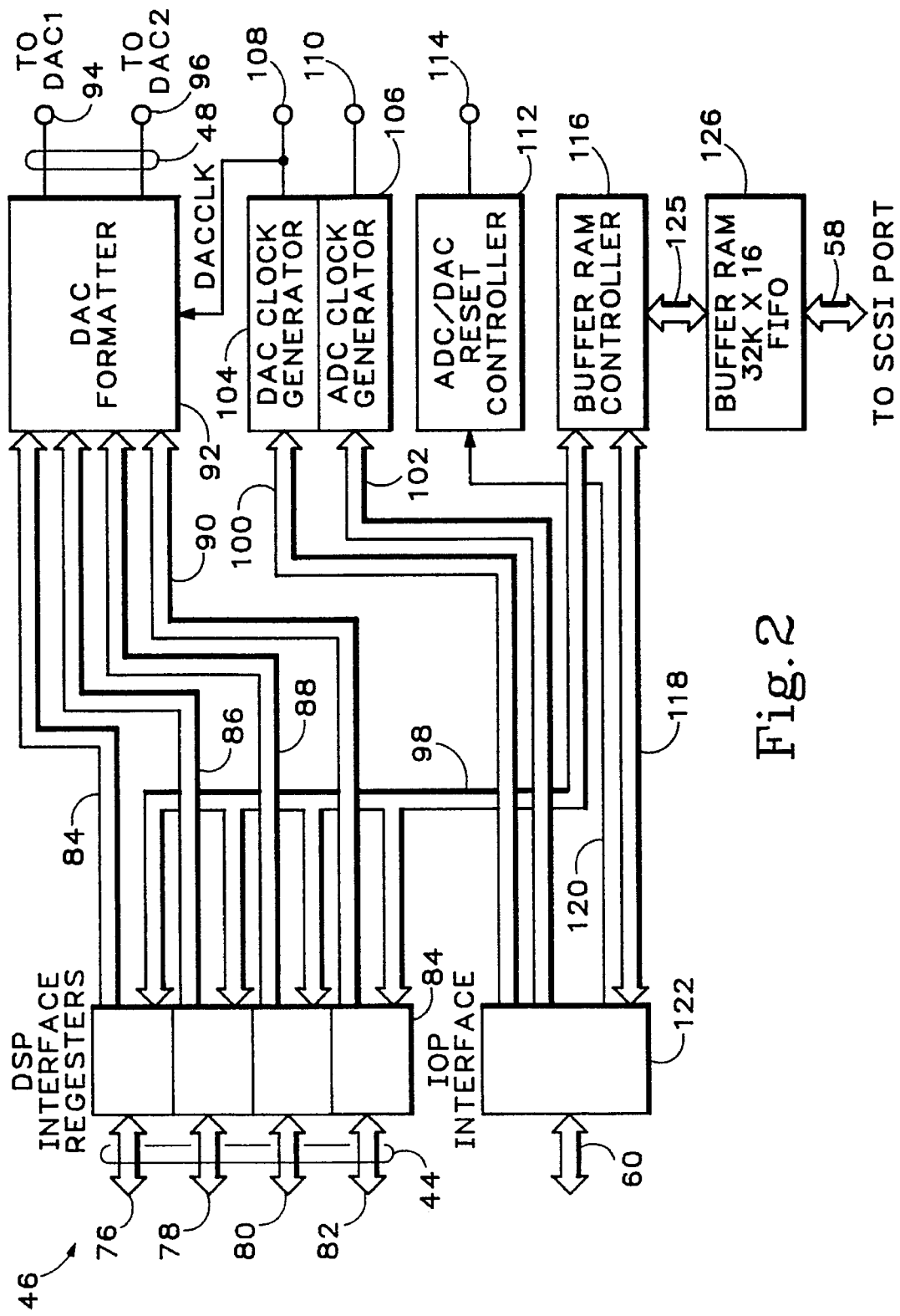
FIG. 2 is a block diagram of data formatter 46 shown in FIG. 1 implemented as an integrated circuit.

Referring now to FIG. 2, a block diagram of the data formatter 46 of FIG. 1 is shown. In the preferred embodiment, formatter 46 is implemented as an integrated circuit ("IC") gate array. Processed digital outputs 44, in FIG. 1, are comprised of four separate bidirectional busses 76, 78, 80, and 82, one for each digital signal processor. The bidirectional busses 76, 78, 80, and 82 connect to a corresponding set of DSP interface registers 84, one set connected to each bidirectional bus. In the preferred embodiment, each DSP 42, in FIG. 1, interfaces with a set of read/write registers used to transfer data to and from a buffer ram 126, the other three DSP's and a DAC formatter 92. Additionally, some registers are used for control functions.

Each register set is connected to DAC formatter 92 through a corresponding DAC interface bus 84, 86, 88, and 90. The DAC interface busses pass the processed digital data from the respective digital signal processor to the DAC formatter 92. The DAC formatter 92 interleaves and serializes the processed digital data received from two DAC interface busses onto a single serial data line, either 94 or 96, with the other two DAC interface busses being output in a similar manner on the remaining serial data line. The DAC formatter 92 receives a clock signal 108 from DAC clock generator 104, which clocks out serial data output on the serial data lines 94 and 96.

An I/O processor (IOP) interface 122 interfaces the data formatter to the I/O processor (not shown in FIG. 2) through IOP bus 60. The IOP interface 122 directs the data present on IOP bus 60 to the appropriate destination. The IOP interface 122 can direct the data on IOP bus 60 to DAC clock generator 104 over bus 100, or to ADC clock generator 106 over bus 102. In this way, I/O processor 70 (in FIG. 1) can write data to DAC clock generator 104 to establish the necessary clock frequency on DAC clock 108 and, similarly, can write data to ADC clock generator 106 to establish the necessary clock frequency on ADC clock 110. IOP interface 122 also interfaces to a buffer RAM controller 116 over bidirectional buffer RAM controller bus 118. IOP interface 122 can send or receive data from the buffer RAM controller 116 over bidirectional buffer RAM controller bus 118. 10P interface 122 also provides reset line 120 connected to ADC/DAC reset controller 112, which, in turn, produces reset output 114.

Buffer RAM controller 116 is connected to all four sets of buffer RAM registers in DSP interface registers 84 via bus 98. Buffer RAM controller 116 is also connected to buffer RAM 126 through RAM controller bus 125. Communication between the DSP interface registers 84 and buffer RAM 126 and between the IOP interface 122 and buffer RAM 126 is controlled by buffer RAM controller 116. The buffer RAM controller 116 is responsible for sequentially polling the DSP and IOP interface registers and transferring any data found thereby to RAM buffer 126. Also, the buffer RAM controller 116 receives data from the buffer RAM 126 and transfers the data to the appropriate DSP interface register. In addition, the buffer RAM controller coordinates transfers of data to and from IOP interface 122. Buffer RAM 126 is connected directly to SCSI port through RAM bus 58. In the preferred embodiment, buffer RAM 126 is a 32K ×16 dual ported bidirectional first-in-first-out (FIFO) RAM, which can be included as part of the data formatter 46 IC or as a stand-alone IC such as µPD42532 manufactured by NEC of Mountain View, Calif.

Figure 3:
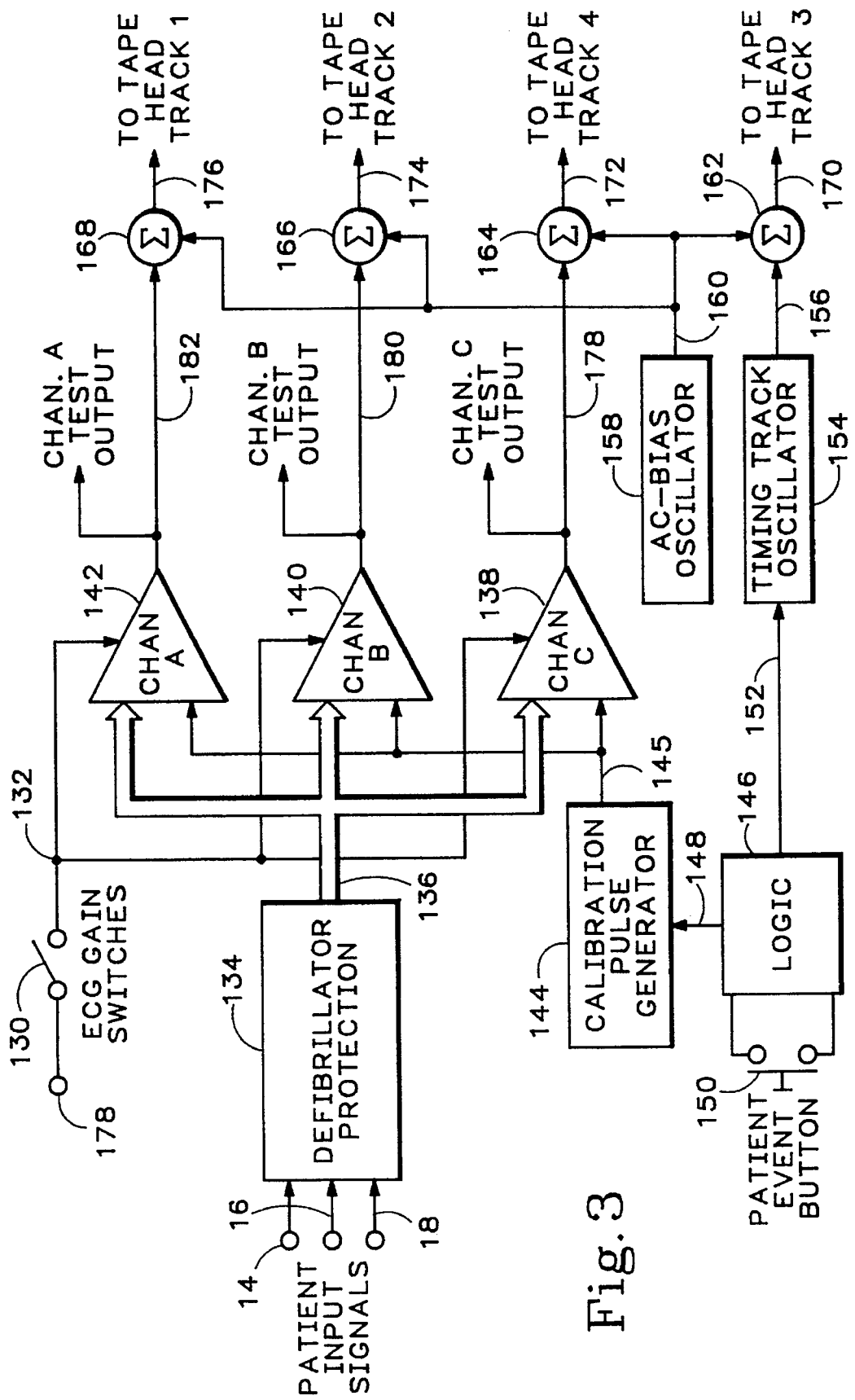
FIG. 3 is a detailed block diagram of the Holter recorder shown in FIG. 1.

Turning now to FIG. 3, recorder 12 of FIG. 1 is shown in greater detail. The patient signals 14, 16, and 18, which are each differential inputs, are received by a defibrillator protection network 134, which provides protection for both the recorder and the patient in the event of a patient being defibrillated while connected to the recorder. The outputs 136 consist of three differential signal pairs from network 134.

Each pre-emphasis amplifier 138, 140, and 142 receives a gain setting signal on line 132 from ECG gain switch 130. The gain switch 130 allows the gain of each amplifier to be individually set to one of two present values. Pre-emphasis amplifiers 138, 140, and 142 also receive calibration and characterization signals over output lines 145 from a calibration pulse generator 144. The calibration pulse generator is connected to a logic circuit 146 through input lines 148. Control signals are transmitted on input lines 148 during a characterization/calibration period. Calibration pulse generator 144 transmits characterization and calibration signals on output lines 145 for approximately the first 8 ½ minutes after the recorder power is turned on.

Patient event button 150 is connected to logic circuit 146. Event button 150 is pressed by the patient during a physical event that the patient wishes to note. When event button 150 is pressed, logic circuit 146 amplitude-modulates timing track oscillator 154 with control signal 152. The amplitude modulation of oscillator 154 is used to indicate a patient event on the timing track.

Pre-emphasis amplifiers 138, 140, and 142 have single-ended outputs 178, 180, and 182, respectively, which are connected to summers 164, 166, and 168, respectively, as well as being supplied as output test channels. The single-ended outputs 178, 180, and 182 are combined with an AC-bias signal on bias line 160 produced by an AC-bias oscillator 158. The AC-bias signal is required in head output lines 172, 174, and 176 in order for the head output signals to be properly recorded by the tape head. Similarly, oscillator output 156 is combined with AC-bias signal 160 by summer 162 to produce head output line 170. Summers 162, 164, 166, and 168 are implemented with passive networks, described in detail below.

Figure 4:
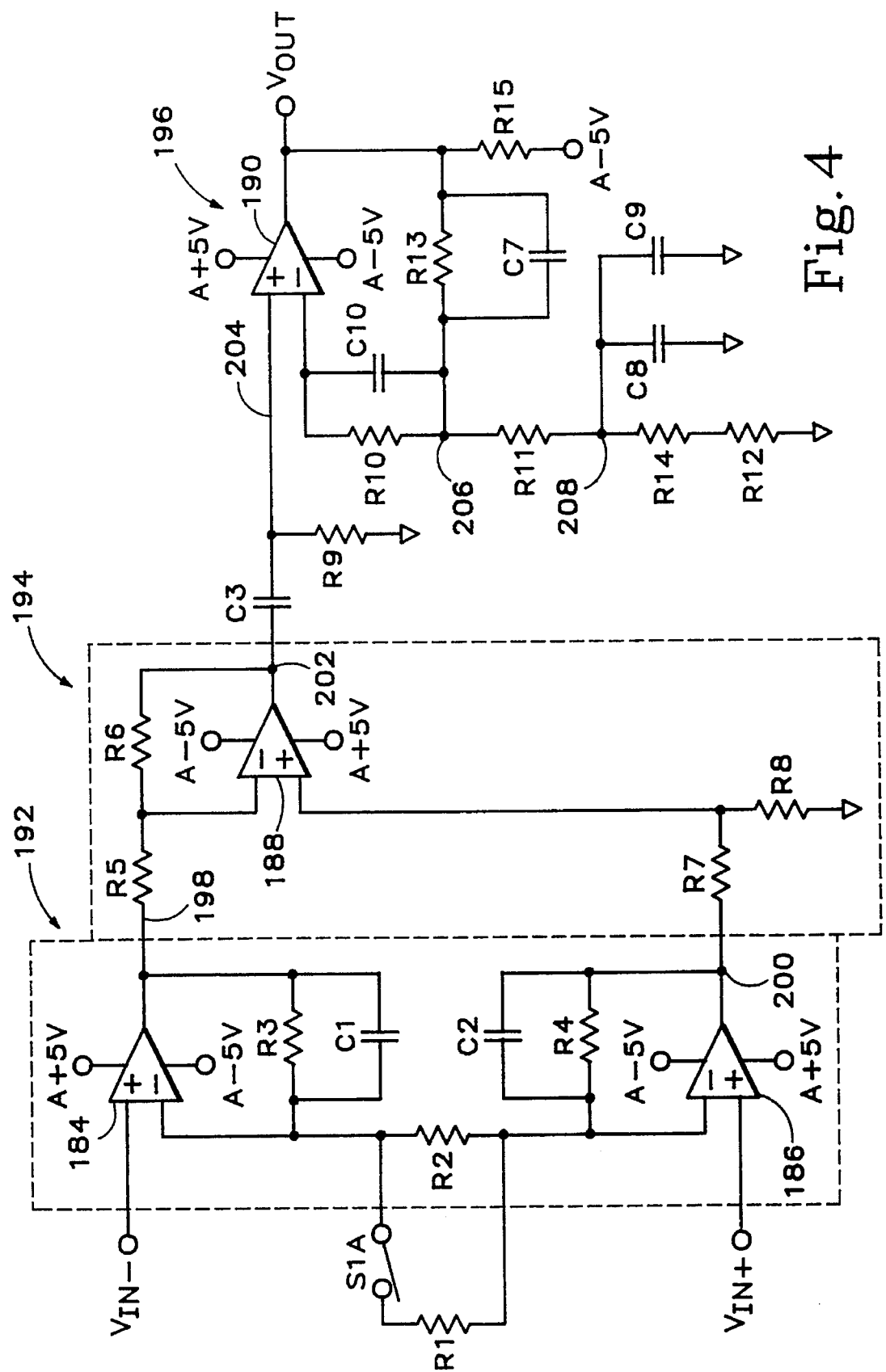
FIG. 4 is a detailed schematic of an individual pre-emphasis amplifier contained in the recorder of FIG. 1.

Referring to FIG. 4, a detailed schematic of an individual pre-emphasis amplifier, i.e., 138, 140, and 142 of FIG. 3, is shown. The pre-emphasis amplifier is comprised of three separate stages: a differential amplifier 192 having a predetermined high frequency rolloff, a differential input (VIN+ and VIN−) and a differential output (198 and 200); a differential-to-single-ended converter 194 having a differential input coupled to the output of the differential amplifier and an output 202; and an output amplifier 196 having a predetermined high frequency boost, an input coupled to the output of the differential-to-single-ended converter, and an output for providing a single-ended boosted voltage.

The differential amplifier stage 192 receives a differential input signal consisting of a positive input VIN+ and a negative input VIN−. The differential amplifier stage 192 has a first operational amplifier ("op-amp") 184 and a second operational amplifier 186 coupled to the negative input VIN+ and the positive input VIN+, respectively. The negative input VIN− is connected to the positive input of the first op-amp 184. Coupled between the negative input and the output of the first op-amp 184 is a first feedback network, consisting of a parallel combination of resistor R3 and capacitor C1. Similarly, the positive input of the second op-amp 186 is connected to the positive input VIN+. Coupled between the negative input and the output of the second operational amplifier 186 is a second feedback network, consisting of the parallel combination of resistor R4 and capacitor C2. In the preferred embodiment, resistors R3 and R4 are about 4.64 KΩ and capacitors C1 and C2 are about 0.1 μF to produce a rolloff frequency of about 300 hertz. The output 198 of the first op-amp 184 and the output of the second op-amp 186 form the differential output of differential output stage 192.

Coupled between the negative inputs of the first and second op-amps 184 and 186 is a third network comprising a first resistor R2; a second resistor R1; and a switch S1A for coupling either the first resistor, or the parallel combination of the first and second resistors, to the negative inputs of the first and second op-amps. In the preferred embodiment, first resistor R2 is about 2.15 KΩ and second resistor R1 is about 1.78 KΩ. When switch S1A is open, the first resistor R2 is coupled between the negative inputs of first 184 and second 186 op-amps. When switch S1A is closed, however, the parallel combination of first resistor R2 and second resistor R1 is coupled between the negative inputs of first 184 and second 186 op-amps. Thus, the gain of the differential input stage 192 can be set to two distinct settings by opening or closing the switch S1A. In the preferred embodiment, using the values indicated above, the gain of the differential input stage is reduced by about one-half when switch S1A is open.

The differential output 198, 200 of differential input stage 192 is coupled to a differential-to-single-ended converter 194. The differential-to-single-ended converter 194 includes an op-amp 188 and four gain-setting resistors. The first differential output 198 is coupled to the negative input of op-amp 188 through a first resistor R5. A second resistor R6 is coupled between the negative input and the output of op-amp 188. The second differential output 200 is coupled to the positive input of op-amp 188 through a third resistor R7. A fourth resistor R8 is coupled between the positive input of op-amp 188 and ground. In the preferred embodiment, the first, second, third, and fourth resistors are about 10KΩ, and the overall gain of converter 194 is unity.

The single-ended output 202 is AC-coupled to output amplifier 196 through high-pass resistor-capacitor network including resistor R9 and capacitor C3. Coupling capacitor C3 is coupled between single-ended output 202 and output amplifier 196 input 204. Resistor R9 is coupled between the input of output amplifier 196 and ground. In the preferred embodiment, coupling capacitor C3 is comprised of four parallel 1 μF capacitors, and resistor R9 is about 825 KΩ.

Output amplifier 196 is comprised of an operational amplifier 190 having a positive input forming the input to the output amplifier, a negative input, and an output forming the output of the output amplifier $V_{OUT}$. A capacitor C10 and a resistor R10 are coupled to the negative input of op-amp 190 and to a node 206. The parallel combination of resistor R13 and a capacitor C7 is coupled between the output of op-amp 190 and node 206. Coupled between node 206 and node 208 is resistor R11, and coupled between node 208 and ground is the parallel combination of resistor R12 and R14 in a first leg, capacitance C8 in a second leg, and capacitance C9 in a third leg.

The parallel combination of the three legs introduces a zero in the frequency response of the output of output amplifier 196. In the preferred embodiment, resistor R12 is about 9.09 KΩ, R14 is about 422 Ω, capacitance C8 is about 0.68 μF, and capacitance C9 is about 0.47 μF producing a rolloff frequency of about 30 hertz. This results in a greater gain at the higher frequencies than the lower frequencies, referred to herein as pre-emphasis. A pole is introduced by the parallel combination of resistor R13 and capacitance C7, leveling out the frequency response at the corresponding rolloff frequency. In the preferred embodiment, resistor R13 is about equal to 196 KΩ and capacitance C7 is about 4700 pF, producing a rolloff frequency of about 170 Hz. The overall gain of the amplifier increases gradually above 10 hertz to a peak of about 10 dB of gain at about 150 hertz. If pre-emphasis is not desired, capacitors C8 and C9 can be removed from the circuit.

Having described and illustrated the principles of the invention in a preferred embodiment thereof, it is apparent to those skilled in the art that the invention can be modified in arrangement and detail without departing from such principles. I therefore claim all modifications and variation coming within the spirit and scope of the following claims.

We claim:

1. A recorder, comprising:

a plurality of patient monitor lines for connecting a plurality of electrodes attached to a patient to said recorder;

said recorder for recording ECG signals on an audio tape for later playback on a playback system, said recorder and said playback system accounting for losses in said ECG signals, said ECG signals sensed by said electrodes attached to said patient, said ECG signals having an ECG signal amplitude and an ECG signal frequency, said recorder further comprising:

an amplifier including a pre-emphasis gain boost characteristic for selectively boosting the amplitude of the ECG signals within a predetermined frequency range as a function of the ECG signal frequency and not the ECG signal amplitude prior to recording to compensate for said losses in the ECG signals due to the recording and playback of the ECG signals.

2. The unit of claim 1, wherein the amplifier has an amplifier gain that increases gradually above 10 hertz to a peak of about 10 dB of gain at about 150 hertz.

3. A recorder, comprising:

a plurality of patient monitor lines for connecting a plurality of electrodes attached to a patient to said recorder;

said recorder for recording ECG signals on an audio tape for later playback on a playback system, said recorder and said playback system accounting for losses in said ECG signals, said ECG signals sensed by said electrodes attached to said patient, said ECG signals having an ECG signal amplitude and an ECG signal frequency, said recorder further comprising:

an amplifier including a pre-emphasis gain boost characteristic for selectively boosting the amplitude of the ECG signals within a predetermined frequency range as a function of the ECG signal frequency and not the ECG signal amplitude prior to recording to compensate for said losses in the ECG signals due to the recording and playback of the ECG signals, said amplifier further comprising:

a differential amplifier having a predetermined high frequency rolloff, the differential amplifier having a differential input for receiving the ECG signals and a differential output;

a differential-to-single-ended converter having a differential input coupled to the output of the differential amplifier and an output; and an output amplifier having a predetermined high frequency boost, the output amplifier having an input coupled to the output of the differential-to-single-ended converter and an output for providing the boosted ECG signals.

4. The unit of claim 3, wherein the differential amplifier comprises a first operational amplifier having a positive input, a negative input, and an output;

a first resistor and first capacitor connected in parallel and coupled between the output and the negative input of the first operational amplifier;

a second operational amplifier having a positive input, a negative input, and an output;

a second resistor and second capacitor connected in parallel and coupled between the output and the negative input of the second operational amplifier, wherein the positive inputs of the first and second operational amplifiers form the differential input and the outputs of the first and second operational amplifiers form the differential output.

5. A method for recording ECG signals on an audio tape for later playback on a playback system, said recorder and playback system accounting for losses in said ECG signals, said ECG signals having an ECG signal amplitude and an ECG signal frequency, said method comprising the steps of:

sensing the ECG signals on electrodes attached to a patient, thereby creating sensed signals;

boosting the amplitude of the sensed signals within a predetermined frequency range as a function of the EGG signal frequency and not the ECG signal amplitude to compensate for said losses of the ECG signals due to the recording and playback of the ECG signals, thereby creating boosted signals, wherein said sensed signals outside of said predetermined range are unboosted signals; and recording the boosted and unboosted signals, thereby creating recording signals.

* * * * *